(12) United States Patent  (10) Patent No.: US 10,399,916 B2
Tomiyori et al.  (45) Date of Patent: Sep. 3, 2019

(54) METHOD OF PRODUCING HYDROFLUOROOLEFIN

(71) Applicant: AGC Inc., Chiyoda-ku (JP)

(72) Inventors: Yusuke Tomiyori, Chiyoda-ku (JP); Masahiko Nakamura, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 16/007,051

(22) Filed: Jun. 13, 2018

(65) Prior Publication Data

US 2018/0290951 A1  Oct. 11, 2018

Related U.S. Application Data

(63) Continuation of application No. PCT/JP2016/087637, filed on Dec. 16, 2016.

(30) Foreign Application Priority Data

Dec. 16, 2015  (JP) ................................. 2015-245495

(51) Int. Cl.
 *C07C 17/25* (2006.01)
 *C07C 21/18* (2006.01)
 (Continued)

(52) U.S. Cl.
 CPC ............ *C07C 17/25* (2013.01); *C07C 17/38* (2013.01); *C07C 21/18* (2013.01); *C07B 61/00* (2013.01)

(58) Field of Classification Search
 CPC .................................................. C07C 17/25
 See application file for complete search history.

(56) References Cited

U.S. PATENT DOCUMENTS 5,856,593 A  1/1999  Powell et al.
8,658,846 B2 *  2/2014  Knapp ................. C07C 17/383
  570/178
(Continued)

FOREIGN PATENT DOCUMENTS

CN  101133008  2/2008
CN  101563308  10/2009
(Continued)

OTHER PUBLICATIONS

WO2015/147063A1, Oct. 2015, Effectively filed Mar. 27, 2014, pp. 1-21; English translation (Year: 2014).*
(Continued)

*Primary Examiner* — Medhanit W Bahta
(74) *Attorney, Agent, or Firm* — Oblon, McClelland, Maier & Neustadt, L.L.P.

(57) ABSTRACT

There is provided a method of producing HFO with which diluent gas is easily separated even at a low boiling point and which has excellent productivity. A method of producing HFO includes: converting HFC of the formula (1) into the HFO of the formula (2) to obtain a first gas composition containing the HFO and the fluorine-containing solvent, $CR^1R^2X^1CR^3R^4X^2$ (1), $CR^1R^2{=}CR^3R^4$ (2), where in the formulae, $R^1$ to $R^3$ are H or F, $R^4$ is H, F, $CH_3$, $CH_2F$, $CHF_2$ or $CF_3$, the total number of fluorine atoms of $R^1$ to $R^4$ is one or more, and the total number of hydrogen atoms of $R^1$ to $R^4$ is one or more. One of $X^1$ and $X^2$ is H, and the other of $X^1$ and $X^2$ is F; and separating the fluorine-containing solvent from the first gas composition to obtain a second gas composition containing the HFO.

18 Claims, 1 Drawing Sheet

(51) Int. Cl.
*C07C 17/38* (2006.01)
*C07B 61/00* (2006.01)

(56) References Cited

U.S. PATENT DOCUMENTS

| | | |
|---|---|---|
| 2006/0094911 A1 | 5/2006 | Rao et al. |
| 2006/0116538 A1 * | 6/2006 | Miller .................... C07C 17/25 570/178 |
| 2010/0145111 A1 | 6/2010 | Sharratt et al. |
| 2011/0112338 A1 | 5/2011 | Smith et al. |
| 2013/0035526 A1 | 2/2013 | Elsheikh et al. |
| 2013/0068989 A1 | 3/2013 | Mahler et al. |
| 2016/0046546 A1 * | 2/2016 | Peng ...................... C07C 17/25 570/156 |

FOREIGN PATENT DOCUMENTS

| | | |
|---|---|---|
| CN | 102026947 | 4/2011 |
| CN | 102858725 | 1/2013 |
| JP | 10-505337 | 5/1998 |
| JP | 11-292807 | 10/1999 |
| JP | 2008-518938 | 6/2008 |
| JP | 2010-513437 | 4/2010 |
| JP | 2011-520856 | 7/2011 |
| JP | 2013-523882 | 6/2013 |
| KR | 10-2008-0066844 | 7/2008 |
| KR | 10-2011-0040758 | 4/2011 |
| WO | WO 2006/050215 A2 | 5/2006 |
| WO | WO 2008/075017 A2 | 6/2008 |
| WO | 10-2009-0090351 | 8/2009 |
| WO | WO 2009/138764 A1 | 11/2009 |
| WO | WO 2011/130108 A1 | 10/2011 |
| WO | WO-2015147063 A1 * | 10/2015 ............. C07C 17/25 |

OTHER PUBLICATIONS

International Search Report dated Feb. 7, 2017 in PCT/JP2016/087637 filed Dec. 16, 2016 (with English Translation).
Written Opinion dated Feb. 7, 2017 in PCT/JP2016/087637 filed Dec. 16, 2016.

* cited by examiner

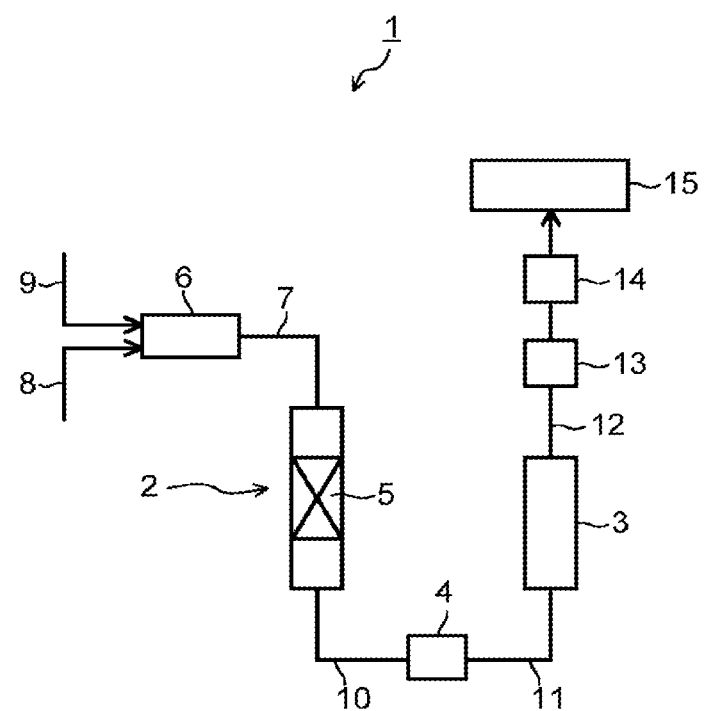

METHOD OF PRODUCING HYDROFLUOROOLEFIN

CROSS-REFERENCE TO RELATED APPLICATIONS

This application is a continuation of prior International Application No. PCT/JP2016/087637, filed on Dec. 16, 2016 which is based upon and claims the benefit of priority from Japanese Patent Application No. 2015-245495, filed on Dec. 16, 2015; the entire contents of all of which are incorporated herein by reference.

FIELD

The present invention relates to a method of producing hydrofluoroolefin, and particularly relates to a method of efficiently producing hydrofluoroolefin from hydrofluorocarbon.

BACKGROUND

Hydrofluoroolefin (HFO) such as trifluoroethylene (HFO-1123) and 2,3,3,3-tetrafluoropropene (HFO-1234yf) has a small global warming potential (GWP), so that in recent years, it has been largely expected as a new refrigerant which takes the place of difluoromethane (HFC-32) and 1,1,1,2,2-pentafluoroethane (HFC-125) being greenhouse effect gas.

Conventionally, as a method of producing HFO-1123, there has been known a method in which relatively inexpensive 1,1,1,2-tetrafluoroethane (HFC-134a) is used as a raw material. Further, as a method of producing HFO-1234yf, there has been known a method in which hydrofluorocarbon (HFC) such as 1,1,1,2,2-pentafluoropropane (HFC-245cb) or 1,1,1,2,3-pentafluoropropane (HFC-245eb) is used as a raw material.

For example, Reference 1 (JP-A H10-505337) discloses a method of producing HFO-1123 by causing dehydrofluorination reaction of HFC-134a while using metal fluoride or metal oxide as a catalyst. In the method of producing disclosed in Reference 1 (JP-A H10-505337), HFC-134a being a raw material and source gas containing nitrogen gas as diluent gas are supplied to a heating reaction band, and the dehydrofluorination reaction of HFC-134a is caused in the presence of catalyst in the heating reaction band, to thereby produce a composition containing HFO-1123.

SUMMARY

However, in the producing method disclosed in Reference 1 (JP-A H10-505337), the obtained composition contains HFO-1123 and the nitrogen gas which is the diluent gas of HFC-134a being the raw material. A boiling point of HFO-1123 is low, so that severe conditions of low temperature and high pressure become necessary to separate HFO-1123 and the nitrogen gas in the composition. For this reason, when the nitrogen gas is used as the diluent gas, equipment enabling a low-temperature and high-pressure state in a reactor becomes necessary to separate HFO-1123 and the nitrogen gas after the reaction. Further, the equipment as above results in quite high production cost such as an electric bill.

Specifically, when the severe conditions as described above are not achieved at the time of separating HFO-1123 and the nitrogen gas, it is not possible to separate HFO-1123 and the nitrogen gas. For this reason, in the producing method disclosed in Reference 1 (JP-A H10-505337), a refinement efficiency of HFO-1123 is too low, so that when industrial mass production is tried to be realized, for example, practicality thereof is quite low.

A problem to be solved by the present invention is to provide a method of producing HFO capable of easily separating HFO and diluent gas even when a boiling point (normal boiling point) of HFO which is a compound being an object of manufacture is low, and excellent in productivity.

Note that in the present specification, abbreviated names of halogenated hydrocarbon compounds are described in parentheses after the compound names, and in the present specification, the abbreviated names are employed in place of the compound names according to need. Further, when a compound name or an abbreviated name is described without making any mention, the compound name and the abbreviated name indicate to be an E-isomer and/or a Z-isomer. Further, when (E) is added after the compound name or the abbreviated name, it means that the compound name or the abbreviated name indicates an E-isomer, and when (Z) is added after the compound name or the abbreviated name, it means that the compound name or the abbreviated name indicates a Z-isomer. Further, saturated hydrofluorocarbon is referred to as HFC, and is used in distinction from HFO.

The present invention provides a method of producing HFO having a configuration described in the following [1] to [13].

[1] A method of producing HFO, including:
a reaction step of converting, in the presence of fluorine-containing compound having a normal boiling point higher than a normal boiling point of HFO represented by the following formula (2), HFC represented by the following formula (1) into the HFO represented by the following formula (2), to obtain a first gas composition containing the HFO and the fluorine-containing compound,

$$CR^1R^2X^1CR^3R^4X^2 \quad (1)$$

$$CR^1R^2=CR^3R^4 \quad (2)$$

where, in the formula (1) and the formula (2), $R^1$ to $R^3$ are each independently a hydrogen atom or a fluorine atom, $R^4$ is a hydrogen atom, a fluorine atom, $CH_3$, $CH_2F$, $CHF_2$ or $CF_3$, the total number of fluorine atoms of $R^1$ to $R^4$ is one or more, and the total number of hydrogen atoms of $R^1$ to $R^4$ is one or more, and one of $X^1$ and $X^2$ is a hydrogen atom, and the other of $X^1$ and $X^2$ is a fluorine atom; and a separation step of separating the fluorine-containing compound from the first gas composition to obtain a second gas composition containing the HFO, in which in the reaction step, the fluorine-containing compound is inert and in a gaseous state.

[2] In the method of producing HFO described in [1], the fluorine-containing compound is: a saturated or unsaturated hydrocarbon compound having a carbon number of 4 to 10; or a saturated or unsaturated organic compound having at least one or more of hetero atoms selected from a group consisting of an oxygen atom, a sulfur atom, a selenium atom, and a nitrogen atom at a position between a carbon atom and a carbon atom of the hydrocarbon compound, the fluorine-containing compound has fluorine atoms substituted for a part or all of hydrogen atoms; out of two adjacent carbons in the fluorine-containing compound, one has a carbon-fluorine bond and the other does not have a carbon-hydrogen bond; and the number of fluorine atoms contained in the fluorine-containing compound is 45% or more in terms of element concentration in the fluorine-containing compound.

[3] In the method of producing HFO described in [1] or [2], a difference between the normal boiling point of the fluorine-containing compound and the normal boiling point of the HFO is 10° C. or more.

[4] In the method of producing HFO described in any one of [1] to [3], the fluorine-containing compound contains at least one kind selected from a group consisting of perfluorocarbon, perfluoroalkyl ether, alkyl perfluoroalkyl ether, perfluoroalkyl thioether, alkyl perfluoroalkyl thioether, perfluoroalkene, and a perfluoroaromatic compound.

[5] In the method of producing HFO described in any one of [1] to [4], the fluorine-containing compound contains at least one kind selected from a group consisting of perfluoropentane, perfluoro-2-methylpentane, perfluorohexane, perfluoro-2-methylhexane, perfluoroheptane, perfluorocyclohexane, perfluoromethylcyclohexane, perfluorobenzene, perfluorotoluene, perfluoroethyl perfluorobutyl ether, perfluoroethyl perfluoropentyl ether, ethyl perfluorobutyl ether, propyl perfluorobutyl ether, and ethyl perfluoropentyl ether.

[6] In the method of producing HFO described in any one of [1] to [5], the separation step includes a step of separating the fluorine-containing compound contained in the first gas composition by liquefying the fluorine-containing compound under a pressure of not less than −0.1 MPa nor more than 4.0 MPa and a temperature of not less than −30° C. nor more than 100° C.

[7] In the method of producing HFO described in any one of [1] to [6], a molar ratio between the HFC and the fluorine-containing compound (HFC/fluorine-containing compound) in the reaction step is not less than 0.5/99.5 nor more than 60/40.

[8] In the method of producing HFO described in any one of [1] to [7], the HFC is 1,1,1,2-tetrafluoroethane, and the HFO is trifluoroethylene.

[9] In the method of producing HFO described in any one of [1] to [7], the HFC is 1,1,1,2,2-pentafluoropropane and/or 1,1,1,2,3-pentafluoropropane, and the HFO is 2,3,3,3-tetrafluoropropene.

[10] In the method of producing HFO described in any one of [1] to [9], the reaction step includes a step of making the HFC and a catalyst to be brought into contact with each other.

[11] In the method of producing HFO described in [10], the catalyst contains at least one kind selected from a group consisting of metal, metal oxide, and metal halide.

[12] In the method of producing HFO described in [10] or [11], the catalyst contains at least one kind selected from a group consisting of iron, zinc, cobalt, nickel, palladium, platinum, iridium, rhodium, ruthenium, chromium oxide, aluminum oxide, zinc oxide, zirconium oxide, niobium oxide, tin oxide, titanium oxide, iron oxide fluoride, aluminum fluoride, aluminum chloride, chromium fluoride, chromium chloride, and silicon oxide.

[13] In the method of producing HFO described in any one of [1] to [12], a temperature to convert the HFC into the HFO is not less than 200° C. nor more than 1200° C.

According to embodiments of the present invention, it is possible to provide a method of producing HFO capable of easily separating HFO and diluent gas of HFC being a raw material even when a boiling point (normal boiling point) of HFO is low, and excellent in productivity.

BRIEF DESCRIPTION OF THE DRAWINGS

The FIGURE is a schematic view illustrating one example of a reaction device used for a method of producing HFO according to the present invention.

DETAILED DESCRIPTION

Hereinafter, embodiments of the present invention will be described.

A method of producing HFO being an embodiment of the present invention includes the following reaction step and separation step.

Reaction step: a step of converting, in the presence of fluorine-containing compound (referred to as "fluorine-containing compound (Q)", hereinafter) having a normal boiling point higher than a normal boiling point of HFO represented by the following formula (2) (referred to as "HFO (2)", hereinafter), at least one kind of HFC represented by the formula (1) (referred to as "HFC (1)", hereinafter) into the HFO (2), to obtain a first gas composition containing the HFO (2) and the fluorine-containing compound (Q). Separation step: a step of separating the fluorine-containing compound (Q) from the first gas composition to obtain a second gas composition containing the HFO (2).

The formula (1) is $CR^1R^2X^1CR^3R^4X^2$, and the formula (2) is $CR^1R^2=CR^3R^4$. In the formula (1) and the formula (2), $R^1$ to $R^3$ are each independently a hydrogen atom or a fluorine atom, $R^4$ is a hydrogen atom, a fluorine atom, $CH_3$, $CH_2F$, $CHF_2$ or $CF_3$. Further, the total number of fluorine atoms of $R^1$ to $R^4$ is one or more, and the total number of hydrogen atoms of $R^1$ to $R^4$ is one or more. One of $X^1$ and $X^2$ is a hydrogen atom, and the other of $X^1$ and $X^2$ is a fluorine atom. Specifically, when $X^1$ is the hydrogen atom, $X^2$ is the fluorine atom, or when $X^1$ is the fluorine atom, $X^2$ is the hydrogen atom.

In the reaction step, a reaction in which the HFO (2) represented by the formula (2) is generated from the HFC (1) represented by the formula (1) can be represented by the following reaction formula (3).

[Chemical Formula 1]

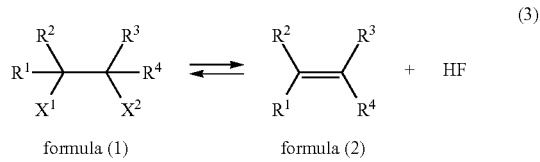

formula (1)　　　　formula (2)

When the HFC (1) is properly processed under a predetermined condition, a dehydrofluorination reaction in which $X^1$ and $X^2$ of the HFC (1) are simultaneously eliminated occurs. According to the dehydrofluorination reaction of the HFC (1) represented by the reaction formula (3) as above, the HFO (2) and hydrogen fluoride are simultaneously generated.

In the method of producing HFO of the present embodiment, the numbers of carbons of the HFC (1) and the HFO (2) are each two to three.

In the method of producing HFO of the present embodiment, the normal boiling point of the compound represented by the formula (2) being an object is preferably −104 to 32° C., and more preferably less than 0° C.

In the method of producing HFO of the present embodiment, as a combination in the method of producing the HFO (2) being an object from the HFC (1) being a raw material, there can be cited, for example, a method of producing 1,1-difluoroethylene (HFO-1132a, normal boiling point: −83° C.) from trifluoroethane (1,1,1-trifluoroethane (HFC-143a), 1,1,2-trifluoroethane (HFC-143), or a mixture of HFC-143a and HFC-143), a method of producing trifluoroethylene (HFO-1123, normal boiling point: −56° C.) from tetrafluoroethane (1,1,2,2-tetrafluoroethane (HFC-134), 1,1,1,2-tetrafluoroethane (HFC-134a), or a mixture of HFC-134 and HFC-134a), a method of producing 2,3,3,3-tetrafluoropropene (HFO-1234yf, normal boiling point: −28.3° C.) from pentafluoropropane (1,1,1,2,2-pentafluoropropane (HFC-245cb), 1,1,1,2,3-pentafluoropropane (HFC-245eb), or a mixture of HFC-245cb and HFC-245eb), a method of producing 1,3,3,3-tetrafluoropropene (HFO-1234ze) (trans-1,3,3,3-tetrafluoropropene (HFO-1234ze (E), normal boiling point: −16° C.), cis-1,3,3,3-tetrafluoropropene (HFO-1234ze (Z), normal boiling point: −16° C.), or a mixture of HFO-1234ze (E) and HFO-1234ze (Z)) from pentafluoropropane (1,1,1,3,3-pentafluoropropane (HFC-245fa), 1,1,1,2,3-pentafluoropropane (HFC-245eb), or a mixture of HFC-245fa and HFC-245eb), and so on. Among the above, the method of producing HFO-1123 from HFC-134a, or the method of producing HFO-1234yf from pentafluoropropane (HFC-245cb, HFC-245eb, and a mixture of HFC-245cb and HFC-245eb) is preferable from a point that the HFO (2) can be efficiently manufactured. Note that the boiling points of the above-described HFO-1234ze (Z) and HFO-1234ze (E) are values described in publicly-known documents (Journal of Fluorine Chemistry, Journal of the Chemical Society, and the like).

The method of producing HFO of the present embodiment may be either an all continuous-type producing method where the reaction step and the separation step are continuously carried out, or may be an all batch-type producing method where the reaction step and the separation step are each a batch-type process, as long as the reaction step and the separation step are carried out in this order.

Besides, the reaction step may be either a continuous-type step or a batch-type step. The separation step may also be either a continuous-type step or a batch-type step, similarly to the reaction step. From a viewpoint of reducing time for maintenance and increasing productivity, the separation step of liquefying and separating vaporized fluorine-containing compound (Q), is preferably the continuous-type step.

The method of producing HFO of the present embodiment may further include a step of separating hydrogen fluoride contained in the first gas composition (which is also referred to as "step (A)", hereinafter). The step (A) may be conducted between the reaction step and the separation step, it may be conducted simultaneously with the separation step, or it may be conducted after the separation step. Hydrogen fluoride generated through the reaction formula (3) is separated by the step (A), and thereby, it is possible to reduce loads on refining of the HFO (2) as the object and recovering processes of the HFC (1), the fluorine-containing compound (Q), and so on, which provides excellent productivity.

When the method of producing HFO of the present embodiment also includes the step (A) in addition to the reaction step and the separation step, the method of producing may be the all continuous-type producing method, the all batch-type producing method, or a partial continuous-type producing method where a part of the steps among these steps is the batch-type step, and the other steps are continuously carried out. From a viewpoint of reducing time for maintenance and increasing productivity, the step (A) of separating hydrogen fluoride is preferably the continuous-type step.

Hereinafter, the reaction step, the separation step, and the step (A) will be further described.

<Reaction Step>

In the reaction step, the HFC (1) in the source gas is converted into the HFO (2) in the presence of the fluorine-containing compound (Q). The conversion from the HFC (1) into the HFO (2) is preferably carried out by making the HFC (1) to be brought into contact with a catalyst. When the source gas and the catalyst are brought into contact, the catalyst is preferably in a solid state (solid phase).

Further, regarding supply of the source gas containing the HFC (1) as a reaction component and the fluorine-containing compound (Q) to a reaction field (for example, a heated reactor), both of the source gas and the catalyst may be continuously supplied, or only one of the source gas and the catalyst may be continuously supplied, and the other may be supplied by batch, when the reaction step is the continuous-type step. From a viewpoint of reducing time for maintenance and increasing productivity, it is preferable that the catalyst is supplied to the reactor by batch, and thereafter, the source gas containing the HFC (1) is continuously supplied to the reactor.

Hereinafter, regarding the reaction step, there is described a mode where the source gas in a gas phase is continuously supplied into the reactor, and is brought into contact with the catalyst in the solid phase which is put into the reactor by batch, but, the reaction step in the method of producing HFO of the present embodiment is not limited to such a mode.

(Source Gas)

The source gas contains the HFC (1) being the raw material and the fluorine-containing compound (Q). Further, the source gas may contain other compounds in addition to the HFC (1) and the diluent gas in a range not impairing the effect of the present invention. Besides, the source gas may be partially liquefied. The source gas is preferably a gas composition in which a content ratio of the HFC (1) to the total molar quantity of the compounds contained in the source gas is 1 mol % or more.

The source gas may further contain the HFO (2), in addition to the HFC (1), the fluorine-containing compound (Q), and the other compounds which are contained in an arbitrary manner. Accordingly, when a generated gas composition obtained through various methods of producing HFO contains the HFC (1), the generated gas composition can be used as the source gas in the reaction step. Further, the second gas composition obtained through the method of producing HFO of the present embodiment contains the HFC (1), the HFC (1) may be used as the source gas in the reaction step.

Note that when the HFO (2) is contained in the source gas, the HFO (2) contained in the source gas becomes a factor of causing an reverse reaction of a reaction generating the HFO (2) in a static reaction represented by the reaction formula (3). From such a viewpoint, it is preferable that the HFO (2) is not contained in the source gas. When the HFO (2) is contained, a content ratio of the HFO (2) in the source gas is preferably 0.001 to 55 mol %, more preferably 0.001 to 20 mol %, and the most preferably 0.001 to 5 mol %, with respect to the total molar quantity of the compounds contained in the source gas.

The fluorine-containing compound (Q) in the present embodiment acts as the diluent gas for diluting the HFC (1). The fluorine-containing compound (Q) is a fluorine-containing organic compound being a hydrocarbon compound having a carbon number of 4 to 10 or an organic compound having at least one kind or more of hetero atoms selected from a group consisting of an oxygen atom, a sulfur atom, a selenium atom, and a nitrogen atom at a position between a carbon atom and a carbon atom of the hydrocarbon compound, in which a part or all of hydrogen atoms is/are substituted with fluorine atoms. The fluorine-containing compound (Q) is a compound whose normal boiling point is higher than a normal boiling point of the HFO (2). Further, the fluorine-containing compound (Q) is a compound which is inert and in the gaseous state in the reaction step.

When the fluorine-containing compound (Q) is "inert", this means that the fluorine-containing compound (Q) does not cause the dehydrofluorination reaction in the reaction step. Specifically, there is no chance that, out of two adjacent carbons in the fluorine-containing compound (Q) in the present embodiment, one has a C—F bond and the other has a C—H bond. In such a case, the dehydrofluorination reaction due to the fluorine atom and the hydrogen atom bonded to the adjacent two carbons is not caused, and thus it can be said that the fluorine-containing compound (Q) is "inert". One kind of the fluorine-containing compound (Q) may be used independently, or two or more kinds thereof may be used in combination.

As described above, the fluorine-containing compound (Q) is not limited to the compound containing only carbon, hydrogen, and fluorine as constituent elements, and it may also contain elements such as oxygen, sulfur, selenium, and nitrogen, for example, other than carbon, hydrogen, and fluorine. When the fluorine-containing compound (Q) contains the elements such as oxygen, sulfur, selenium, and nitrogen, these are preferably positioned between the carbon atom and the carbon atom.

The normal boiling point of the fluorine-containing compound (Q) is preferably 0° C. or more. Further, the normal boiling point of the fluorine-containing compound (Q) is preferably higher by 10° C. or more than the normal boiling point of the HFO (2) being the object. The difference in the normal boiling points is preferably 15° C. or more, more preferably 20° C. or more, particularly preferably 30° C. or more, and the most preferably 40° C. or more. As the boiling point of the fluorine-containing compound (Q) becomes higher than the normal boiling point of the object, it becomes easier to separate the fluorine-containing compound (Q) from the first gas composition.

The fluorine-containing compound (Q) may be saturated or unsaturated. Further, the fluorine-containing compound (Q) may be in a chain state, branched, or have a ring structure. The carbon number of the fluorine-containing compound (Q) is preferably not less than 4 nor more than 10, and more preferably not less than 5 nor more than 8.

A fluorine number (n) in the fluorine-containing compound (Q) is a number in a range represented by $m \leq n \leq 2m+2$, in which a carbon number in the fluorine-containing compound (Q) is set to m. The fluorine number in the fluorine-containing compound (Q) is preferably 45% or more, and more preferably 70% or more in terms of element concentration in the fluorine-containing compound.

As the saturated fluorine-containing compound (Q), there can be cited perfluorocarbon, perfluoroalkyl ether, alkyl perfluoroalkyl ether, perfluoroalkyl thioether, alkyl perfluoroalkyl thioether, and so on. As the unsaturated fluorine-containing compound (Q), there can be cited perfluoroalkene, a perfluoroaromatic compound, and so on. The fluorine-containing compound (Q) preferably contains at least one kind selected from a group consisting of the above-described saturated or unsaturated fluorine-containing compounds.

Among the saturated fluorine-containing compounds (Q), as concrete examples of perfluorocarbon, there can be cited perfluoropentane, perfluoro-2-methylpentane, perfluorohexane, perfluoro-2-methylhexane, perfluoroheptane, perfluorocyclohexane, perfluoromethylcyclohexane, and so on. One kind of the saturated fluorine-containing compound (Q) may be used independently, or two or more kinds thereof may be used in combination.

As concrete examples of perfluoroalkyl ether, there can be cited perfluoroethyl perfluorobutyl ether, perfluoroethyl perfluoropentyl ether, and so on.

As concrete examples of alkyl perfluoroalkyl ether, there can be cited ethyl perfluorobutyl ether, propyl perfluorobutyl ether, ethyl perfluoropentyl ether, and so on.

As concrete examples of perfluoroalkyl thioether, there can be cited perfluoroethyl perfluorobutyl thioether, perfluoroethyl perfluoropentyl thioether, and so on.

As concrete examples of alkyl perfluoroalkyl thioether, there can be cited ethyl perfluorobutyl thioether, propyl perfluorobutyl thioether, ethyl perfluoropentyl thioether, and so on.

Among the unsaturated fluorine-containing compounds (Q), as perfluoroalkene, there can be cited perfluoro-2-hexene, perfluorocyclohexene, and so on. As the perfluoroaromatic compound, there can be cited perfluorobenzene, perfluorotoluene, tetrafluorofuran, tetrafluorothiophene, and so on. One kind of the unsaturated fluorine-containing compound (Q) may be used independently, or two or more kinds thereof may be used in combination.

In terms of the efficiency of the separation step and the cost, the fluorine-containing compound (Q) preferably contains at least one kind selected from perfluoropentane, perfluoro-2-methylpentane, perfluorohexane, perfluoro-2-methylhexane, perfluoroheptane, perfluorocyclohexane, perfluoromethylcyclohexane, perfluorobenzene, perfluorotoluene, perfluoroethyl perfluorobutyl ether, perfluoroethyl perfluoropentyl ether, ethyl perfluorobutyl ether, propyl perfluorobutyl ether, and ethyl perfluoropentyl ether. Among the above, perfluoropentane, perfluorohexane, and ethyl perfluorobutyl ether are particularly preferable.

The fluorine-containing compound (Q) can be appropriately selected in accordance with the normal boiling point of the HFO (2) so that the difference between the normal boiling point thereof and the normal boiling point of the HFO (2) falls within the above-described preferable range. For example, when the HFO (2) is HFO-1132a, HFO-1123, HFO-1234yf, HFO-1234ze, or the like, it is preferable to use perfluorohexane (normal boiling point: 56.6° C.), or ethyl perfluorobutyl ether (normal boiling point: 76° C.) as the fluorine-containing compound (Q).

The fluorine-containing compound (Q) is in the gaseous state in the reaction step. In the reaction step, all of the fluorine-containing compound (Q) may be in the gaseous state or a part thereof may be in the gaseous state. In terms of excellence in the conversion ratio of the HFC (1) and in terms of catalytic activity, the entire fluorine-containing compound (Q) is preferably in the gaseous state. Hereinafter, explanation will be made on the method of producing the present embodiment by assuming that the entire fluorine-containing compound (Q) is in the gaseous state in the reaction step, but, the present embodiment is not limited to this.

As a method of supplying the fluorine-containing compound (Q), it is possible to add the fluorine-containing compound (Q) in the reaction step, or when the fluorine-containing compound (Q) is generated as a by-product in the reaction step, it is possible to use the fluorine-containing compound (Q) as a whole or a part of the diluent gas in the reaction step. It is preferable to add the fluorine-containing compound (Q) in the reaction step because an amount of the diluent gas in the reaction step can be adjusted.

Regarding a content ratio of the fluorine-containing compound (Q) in the source gas, it is preferable that a molar ratio between the HFC (1) and fluorine-containing compound (Q) supplied in the reaction step (HFC/fluorine-containing compound (Q)) is 0.5/99.5 to 80/20. In terms of suppression of the deterioration of catalyst, in terms of suppression of the increase in cost due to decomposition of the fluorine-containing compound (Q), and in terms of the improvement in conversion ratio, an upper limit of HFC/fluorine-containing compound (Q) is more preferably 60/40 or less, still more preferably 50/50 or less, and particularly preferably 30/70 or less. Further, in terms of reduction of impurities due to the decomposition of the fluorine-containing compound (Q) and reduction in cost for raising or lowering temperature, a lower limit of HFC/fluorine-containing compound (Q) is more preferably 5/95 or more. When considering the improvement of conversion ratio, the suppression of deterioration of the catalyst, the reduction of the impurities due to the decomposition of vaporized fluorine-containing compound (Q), the cost for raising or lowering the temperature, and the like all together, the molar ratio is particularly preferably 5/95 to 50/50.

Note that in the embodiment where the source gas in the gas phase is continuously brought into contact to be reacted with the catalyst in the solid phase, it is possible to control the molar ratio between the HFC (1) and the fluorine-containing compound (Q) in the source gas by controlling a flow rate per unit time of respective gas phase components and the fluorine-containing compound (Q) in the source gas.

As other compounds capable of being contained in the source gas, except the HFC (1), the fluorine-containing compound (Q), and the HFO (2), there can be cited, for example, impurities derived from a method of producing the HFO (1) or the like, diluent gas other than the fluorine-containing compound (Q), and so on.

As the impurities, there can be cited trifluoromethane (HFC-23), difluoromethane (HFC-32), HFC-134, HFC-143a, HFO-1132a, trans-1,2-difluoroethylene (HFO-1132 (E)), cis-1,2-difluoroethylene (HFO-1132 (Z)), vinyl fluoride (HFO-1141), HFO-1234yf, methane, ethane, ethylene, propane, propylene, acetone, fluorine, hydrogen fluoride, chlorine, hydrogen chloride, and so on (note that except the HFC (1) and the fluorine-containing compound (Q) contained in the source gas, and the HFO (2) being the object).

As diluent gas other than the fluorine-containing compound (Q) capable of being obtained in the source gas, there can be cited gas which is inert with respect to the components contained in the source gas in the reaction step, such as helium, argon, carbon tetrachloride, oxygen, carbon dioxide, and nitrogen gas.

Other compounds in the source gas are preferably not contained from a viewpoint of suppressing the deterioration of catalyst and a viewpoint of suppressing generation of unnecessary by-products to reduce a load on a refining process of HFO performed thereafter. When other compounds are contained, an amount thereof is preferably 0.001 to 40 mol %, more preferably 0.001 to 10 mol %, and the most preferably 0.01 to 1 mol % relative to the total molar quantity of the compounds contained in the source gas.

(Catalyst)

The catalyst used in the reaction step has a catalytic action for the dehydrofluorination reaction of the HFC (1). As the catalyst, there can be cited metal (metal element or alloy), metal oxide, metal halide, and so on, and the catalyst preferably contains at least one kind selected from a group consisting of these. Among these, the metal oxide or the metal halide is preferable because the HFC (1) can be efficiently converted into the HFO (2). One kind of the catalyst may be used independently, or two or more kinds may be used in combination.

As metal forming the metal element, the alloy, the metal oxide, and the metal halide, there can be cited a transition metal element, a group 12 metal element, a group 13 metal element, and a group 14 metal element. In particular, a group 3 metal element, a group 4 metal element, a group 6 metal element, a group 8 metal element, a group 10 metal element, the group 12 metal element, and the group 13 metal element are preferable, and scandium, titanium, zirconium, chromium, iron, zinc, and aluminum are more preferable.

The alloy may be an alloy of two kinds of metals of the above-described metals, or an alloy of three or more kinds of the metals.

The metal oxide may be one kind of oxide of the above-described metals, or a composite oxide of two or more kinds of the metals.

The metal halide may be one kind of halide of the above-described metals, or a composite halide of two or more kinds of the metals.

As the catalyst, concretely, there can be cited iron, zinc, cobalt, nickel, palladium, platinum, iridium, ruthenium, rhodium, titanium oxide, zirconium oxide, chromium oxide, aluminum oxide, zinc oxide, niobium oxide, tin oxide, iron fluoride, aluminum fluoride, aluminum chloride, chromium fluoride, chromium chloride, silicon oxide, and so on, and the catalyst preferably contains at least one kind selected from a group consisting of these. Silica gel is preferable as the silicon oxide. Among them, zinc, platinum, palladium, aluminum oxide, aluminum fluoride, zirconium oxide, and chromium oxide are preferable from a point where the HFC (1) can be efficiently converted into the HFO (2).

A specific surface area of the catalyst measured by a BET method (referred to as a BET specific surface area, hereinafter) is preferably 30 to 400 $m^2/g$. When the BET specific surface area of the catalyst is in the above-described range, the HFC (1) reacts at a high reaction rate, and therefore, a reaction efficiency is good, and in addition to that, a density of particles of the catalyst is not too small, resulting in that the catalyst is difficult to be scattered and has good handleability. The BET specific surface area of the catalyst is more preferably 150 to 400 $m^2/g$.

The catalyst may be supported by a carrier. As the carrier, there can be cited, for example, an alumina carrier, a zirconia carrier, a silica carrier, a silica-alumina carrier, a carbon carrier typified by activated carbon, a barium sulfate carrier, a calcium carbonate carrier, and so on. As the activated carbon, there can be cited, for example, activated carbon prepared from raw materials such as wood, charcoal, fruit shell, palm shell, peat, lignite, and coal. As the carrier, it is preferable to use the alumina carrier.

The catalyst is preferably subjected to activation treatment beforehand from a viewpoint of improving the conversion ratio. As a method of the activation treatment, there can be cited a method where the catalyst is brought into contact with an activation treatment agent in a heated state or unheated state. As the activation treatment agent, there can be cited, for example, oxygen, hydrogen fluoride, hydrogen chloride, a fluorine-containing compound, and so on, and among them, the fluorine-containing compound is preferable. As the fluorine-containing compound, there can be cited, for example, HFC-143, HFC-143a, HFC-134, HFC- 134a, HFC-245cb, HFC-245eb, HFC-245fa, HFO-1132a, HFO-1132 (E), HFO-1132 (Z), HFO-1123, HFO-1234yf, HFO-1234ze, trichlorofluoromethane (HFC-11), dichlorofluoromethane (HFC-21), chlorodifluoromethane (HFC-22), HFC-32, tetrafluoroethylene (FO-14), 1,1,1,2,2-pentafluoroethane (HFC-125), and so on.

It is preferable that the catalyst is subjected to reactivation treatment, in addition to the activation treatment before the reaction as above. Specifically, when the activity of the catalyst is lowered in the conversion reaction, and the conversion ratio of the HFC (1) being the raw material component and selectivity of the HFO (2) being the object are lowered, it is preferable to make the catalyst to be subjected to the reactivation treatment. It is preferable to reuse the catalyst by reproducing the activity of the catalyst through the reactivation treatment.

As a method of the reactivation treatment, there can be cited a method where the catalyst after usage is brought into contact with an activation treatment agent in a heated state or unheated state, in a similar manner to the aforementioned activation treatment which is carried out before usage. As the reactivation treatment agent, it is possible to use a compound similar to the activation treatment agent.

Note that it is preferable to use inert gas such as nitrogen, carbon dioxide, argon, or helium to dilute the activation treatment agent, from points of suppression of a side-reaction, improvement of durability of the catalyst, and so on.

(Reactor and Reaction Conditions)

As a reactor in which the source gas and the catalyst are brought into contact to be reacted in the reaction step, a shape and a structure thereof are not particularly limited as long as it is capable of sustaining later-described temperature and pressure. As the reactor, a cylindrical vertical reactor can be cited, for example. As a material of the reactor, there can be cited glass, iron, nickel, an alloy whose main component is iron or nickel, and so on. The reactor may include a heating unit such as an electric heater heating in the reactor.

The catalyst in the solid phase which is put into the reactor may be accommodated in either form of a fixed bed type or a fluidized bed type. In case of the fixed bed type, either a horizontal fixed bed type or a vertical fixed bed type is available, but, when the source gas is mixed gas composed of multiple components, it is preferable to employ the vertical fixed bed type because occurrence of concentration distribution of each component due to a specific gravity difference is easy to be prevented.

The source gas may be supplied to the reactor at room temperature, but, the source gas is preferably heated before it is supplied to the reactor (preheated), and then supplied so as to increase reactivity in the reactor. When the preheating of the source gas is performed, the source gas can be supplied to the reactor after it is heated to a temperature of preferably 50° C. to 1200° C., and more preferably 50 to 400° C.

When the source gas is preheated to be supplied to the reactor, it is possible that the HFC (1) and the fluorine-containing compound (Q) are separately preheated to be supplied to the reactor, or the HFC (1) and the fluorine-containing compound (Q) are mixed and then preheated to be supplied to the reactor. From a point of simplifying the operation to increase the productivity, it is preferable that the HFC (1) and the fluorine-containing compound (Q) are mixed and then preheated to be supplied to the reactor.

Further, when the HFC (1) and the fluorine-containing compound (Q) are separately preheated, the HFC (1) is preferably preheated to a temperature of 50 to 400° C., and the fluorine-containing compound (Q) is preferably preheated to a temperature of 50 to 400° C. The HFC (1) and vapor may be preheated to the nearly equal temperature or preheated to have a temperature difference. Further, the preheated HFC (1) and fluorine-containing compound (Q) may be mixed and then supplied to the reactor, or they may also be separately supplied to the reactor.

The source gas supplied to the reactor is brought into contact with the catalyst in the solid phase in the reactor. The temperature in the reactor is preferably 200 to 1200° C. from viewpoints of improvement of reactivity and improvement of operating life of the catalyst. Further, from viewpoints of reaction efficiency, suppression of a side-reaction, and production equipment, the temperature in the reactor is more preferably 300 to 1000° C., and more preferably 300 to 800° C. Besides, the pressure in the reactor is preferably not a pressure around a critical point, and concretely, it is preferably −0.1 to 2 MPa, and more preferably −0.1 to 0.5 MPa. A contact time between the source gas and the catalyst in the reactor is preferably from 0.001 to 500 seconds, more preferably from 0.5 to 50 seconds, and particularly preferably from 5 to 30 seconds. Note that in the present specification, the pressure is indicated by a gauge pressure, unless otherwise noted.

(First Gas Composition)

In the reaction step, it is possible to obtain the first gas composition containing the HFO (2), the fluorine-containing compound (Q), and unreacted HFC (1), as outlet gas of the reactor. The first gas composition may contain, other than the HFO (2) being the object, the fluorine-containing compound (Q), and the unreacted HFC (1), the other compounds capable of being contained in the source gas and the by-products generated in the reaction step. As the by-product contained in the first gas composition, there can be cited, for example, HFO-1141, HFO-1132a, HFO-1132 (Z), HFO-1132 (E), HFC-134, HFC-143, HFC-134a, HFC-125, HFC-23, HFC-32, methane, ethylene, ethane, propylene, propane, and so on when the HFC (1) is HFC-134a and the HFO (2) is HFO-1123. Further, the fluorine-containing compound (Q) used as the diluent gas may be partially liquefied.

(Separation Step)

In the separation step, a part or all of the fluorine-containing compound (Q) is separated from the first gas composition to obtain the second gas composition in which a content ratio of the HFO (2) is increased. A method of separating the fluorine-containing compound (Q) is not particularly limited, and can be arbitrary selected according to reaction conditions and reaction products. For example, there can be cited liquefaction through performance of heat removal to the normal boiling point or less of the fluorine-containing compound (Q), liquefaction through performance of heat removal to equal to or less than a boiling point under a pressure in high-pressure conditions, physical absorption where the fluorine-containing compound (Q) is physically dissolved in an absorbing liquid, extractive distillation, and so on. Among these methods, a single method may be used or a plurality of methods may be combined. When a single method is carried out, one-step reaction may be carried out or a reaction may be carried out in several steps. As the method of separating the fluorine-containing compound (Q), the liquefaction through heat removal under a condition of slight pressurization is preferable from a viewpoint of equipment. Note that there is a case where hydrogen fluoride is also separated in addition to the fluorine-containing compound (Q) depending on the separation conditions. For example, when perfluorohexane is subjected to conversion reaction as the fluorine-containing compound (Q), by making the first gas composition pass through an alkaline aqueous solution at room temperature (25° C.), it is possible to separate the first gas composition into three phases of the alkaline aqueous solution in which hydrogen fluoride is dissolved, perfluorohexane, and the second gas composition.

When the fluorine-containing compound (Q) is separated through liquefaction, as conditions for the liquefaction, a pressure is only required to be −0.1 to 4.0 MPa, it is preferably 0.2 MPa or less, and more preferably 0.02 MPa or less. A temperature is preferably −30 to 100° C., more preferably −10 to 100° C., and still more preferably 0 to 90° C.

(Recovery Method of Fluorine-Containing Compound)

It is possible to recover the fluorine-containing compound (Q) separated in the separation step. The recovered fluorine-containing compound (Q) can be reused again as the diluent gas of the reaction step.

(Second Gas Composition)

In the separation step, it is possible to obtain the second gas composition containing the HFO (2) and the unreacted HFC (1). The second gas composition may contain compounds and components which are the same as the other compounds capable of being contained in the aforementioned source gas and the by-products in addition to the HFO (2) being the object and the unreacted HFC (1). In the separation step, the fluorine-containing compound (Q) in the gaseous state contained in the first gas composition is selectively separated. For this reason, the content ratio of the HFO (2) in the second gas composition becomes higher than the content ratio of the HFO (2) in the first gas composition.

The second gas composition can be used for various uses as it is, and it is preferably further refined. As a refining method, there can be cited publicly-known methods such as distillation, adsorption, and washing with an acid aqueous solution, a basic aqueous solution, or a neutral aqueous solution. Substances other than the HFO (2) contained in the second gas composition can be removed and separated to a desired degree by publicly-known methods. The preferable refining method is the method to distillate under an atmospheric pressure, an added pressure, or a reduced pressure. By carrying out the distillation under such a pressure, it is possible to obtain high-purity HFO (2). Further, the unreacted HFC (1) separated from the second gas composition can be recycled as a part of the source gas in the reaction step.

<Step (A)>

Further, the method of producing HFO of the present embodiment preferably includes the step (A) to separate hydrogen fluoride contained in the first gas composition. The step (A) may be performed between the reaction step and the separation step, it may be performed simultaneously with the separation step, or it may be performed after the separation step. Hereinafter, the step (A) will be described regarding a mode in which the step (A) is included between the reaction step and the separation step. When the step (A) is included, an amount of hydrogen fluoride separated in the above-described separation step becomes very small compared to an amount of hydrogen fluoride separated in the step (A).

Although the first gas composition may be supplied to the step (A) as it is, it may be supplied to the step (A) after performing other processes for the first gas composition by providing other process steps between the reaction step and the step (A). Here, other processes mean the processes other than the separations of hydrogen fluoride and the fluorine-containing compound (Q), and not changing compositions of substances other than water contained in the first gas composition. As other processes, there can be cited, for example, processes of storing to a tank, compression by a compressor, heating, cooling, removal of water, and so on.

As the method of separating hydrogen fluoride from the first gas composition in the step (A), there can be cited methods such as distillation, adsorption, neutralization, and a two-phase separation.

The distillation is a method of separating hydrogen fluoride by distilling the first gas composition. The distillation can be carried out under the atmospheric pressure, the added pressure or the reduced pressure, but, it is preferably carried out under the added pressure from a viewpoint of improvement of separation efficiency.

The adsorption is a method in which the first gas composition is brought into contact with an adsorbent so that hydrogen fluoride is adsorbed by the adsorbent to be separated. The adsorbent may be in a solid phase, or may be in a state dispersed in a liquid medium in which the adsorbent is not dissolved (liquid phase). As the adsorbent, sodium fluoride, potassium fluoride, zeolite, activated carbon, and so on can be used. Among them, sodium fluoride is particularly preferable because hydrogen fluoride can be efficiently separated.

The neutralization is a method in which the first gas composition is brought into contact with a basic compound so that hydrogen fluoride is reacted to be separated. The basic compound may be in a solid phase, liquid phase, or gas phase, or may be in a state where it is dispersed in a liquid medium. As the basic compound, sodium hydroxide, potassium hydroxide, potassium bicarbonate, potassium carbonate, ammonia, and so on can be used. Among them, potassium hydroxide is particularly preferable because hydrogen fluoride can be efficiently separated.

The two-phase separation is a method in which the first gas composition is made into a liquid phase under an added pressure to be separated into two phases of an organic phase containing the HFO (2), carbon dioxide, and the HFC (1), and an acid phase containing hydrogen fluoride, and the phase-separated acid phase is separated.

By performing the step (A) where the separation process of hydrogen fluoride is carried out, it is possible to obtain a gas composition whose content ratio of hydrogen fluoride is lower than that of the first gas composition. Specifically, by performing the step (A), it is possible to obtain the gas composition whose content ratio of hydrogen fluoride is low, and which contains the HFO (2), the fluorine-containing compound (Q), and the unreacted HFC (1). When the method of producing HFO of the present embodiment includes the step (A), the gas composition is supplied to the separation step. When the step (A) is included, in the gas composition obtained by the step (A), there is a case where a content ratio of acidic components such as hydrogen chloride and acid fluoride and a content ratio of compounds other than the acidic components contained in the above-described other compounds and by-products are lower than those of the first gas composition.

Note that although the gas composition obtained by the step (A) may be supplied to the separation step as it is, it may be supplied to the separation step after performing other processes for the gas composition by providing other process steps between the step (A) and the separation step. Here, other processes mean the processes other than the separation of the fluorine-containing compound (Q), and not changing compositions of substances other than water contained in the gas composition. As other processes, there can be cited, for example, processes of storing to a tank, compression by a compressor, heating, cooling, removal of water, and so on.

<Reaction Device>

The FIGURE is a schematic view illustrating one example of a reaction device used for the method of producing HFO of the present embodiment. A reaction device 1 includes a reactor 2 including a heating unit such as an electric heater to carry out the reaction step, and a fluorine-containing compound trap 4 to carry out the separation step. Note that the reactor 2 may include a heat removal unit, but, the heat removal unit is not necessarily provided.

Further, the reaction device 1 includes, on a downstream side of the fluorine-containing compound trap 4, a hydrogen fluoride trap 3 to carry out the step (A), a dehydrator 13 to remove water in the second gas composition, a sampling bag 14 which captures the second gas composition, and an analyzer 15 such as gas chromatography (GC) which analyzes components of the second gas composition.

The hydrogen fluoride trap 3 is not necessarily provided. Besides, in the reaction device 1, the hydrogen fluoride trap 3 is arranged between the fluorine-containing compound trap 4 and the dehydrator 13, but, it may be arranged between the reactor 2 and the fluorine-containing compound trap 4.

A catalyst 5 is accommodated in the reactor 2 to form the vertical fixed bed. Further, an upper part being an inlet side of the reactor 2 is connected to a preheating mixer 6 which includes a heating unit such as an electric heater through a source gas supply line 7. It is preferable that the heating unit such as the electric heater is provided also to the source gas supply line 7.

To the preheating mixer 6, a HFC supply line 8 which supplies the HFC (1) and a fluorine-containing compound supply line 9 which supplies the fluorine-containing compound (Q) being the diluent gas are respectively connected. The HFC (1) and the fluorine-containing compound (Q) are respectively introduced into the preheating mixer 6 through the HFC supply line 8 and the fluorine-containing compound supply line 9, mixed and heated to a predetermined temperature in the preheating mixer 6, and then supplied to the reactor 2 through the source gas supply line 7. The HFC supplied to the reactor 2 is brought into contact with the catalyst 5 in the presence of the fluorine-containing compound (Q) in a gaseous state to be converted into the HFO (2). As a result, the first gas composition containing the HFO (2), the fluorine-containing compound (Q), hydrogen fluoride, and the unreacted HFC (1) is obtained. Note that the fluorine-containing compound (Q) may be supplied as it is in a liquid state to the fluorine-containing compound supply line 9, or it may be vaporized beforehand to be supplied to the fluorine-containing compound supply line 9.

Note that it is possible that the HFC supply line 8 and the fluorine-containing compound supply line 9 are coupled before they are connected to the preheating mixer 6, and the HFC (1) and the fluorine-containing compound (Q) are mixed beforehand to be supplied to the preheating mixer 6. Further, at least one of the HFC supply line 8 and the fluorine-containing compound supply line 9 may be equipped with a preheater including an electric heater or the like, and the HFC (1) and fluorine-containing compound (Q) may be supplied to the preheating mixer 6 after preheating at least one of the HFC (1) and the fluorine-containing compound (Q) which is supplied through the line equipped with the preheater.

A lower part of the reactor 2 being an outlet side is connected to the fluorine-containing compound trap 4 through a reactor outlet line 10 which includes a heating unit such as an electric heater. The first gas composition obtained in the reactor 2 is supplied to the fluorine-containing compound trap 4, and when the first gas composition is subjected to heat removal in the outlet line 10 and the fluorine-containing compound trap 4, the fluorine-containing compound (Q) contained in the first gas composition is liquefied. Consequently, the second gas composition as a result of separating the fluorine-containing compound (Q) contained in the first gas composition is obtained.

An outlet of the fluorine-containing compound trap 4 is connected to the hydrogen fluoride trap 3 through an outlet line 11. The second gas composition passed through the fluorine-containing compound trap 4 is supplied to the hydrogen fluoride trap 3 and passed through the hydrogen fluoride trap 3 where the alkaline solution is accommodated, resulting in that hydrogen fluoride contained in the second gas composition is removed. As a result, the second gas composition from which hydrogen fluoride is removed is obtained.

An outlet of the hydrogen fluoride trap 3 is connected to the dehydrator 13 through an outlet line 12. The second gas composition obtained at the hydrogen fluoride trap 3 is supplied to the dehydrator 13, and water contained in the second gas composition is removed. The second gas composition from which water is removed by the dehydrator 13 is collected into the sampling bag 14, and thereafter, components of the second gas composition are analyzed by the analyzer 15 such as the gas chromatography (GC).

According to the method of producing HFO of the present embodiment, it is possible to easily separate HFO and the fluorine-containing compound (Q) being the diluent gas even when the boiling point (normal boiling point) of HFO is low. As a result of this, it is possible to suppress the production cost, and to increase the productivity of HFO.

HFO produced by the producing method of the present embodiment, for example, HFO-1123 or HFO-1234yf is useful as a refrigerant taking over HFC-32 or HFC-125 being the greenhouse effect gas, and as a raw material monomer of a functional material such as a piezoelectric element and film, and as a synthesis intermediate.

EXAMPLES

Hereinafter, the present invention will be described in detail by using examples, but, the present invention is not limited to the following examples.

<Reaction Device>

In examples and comparative examples, a reaction device similar to the reaction device illustrated in the FIGURE (hereinafter, it is referred to as a reaction device (1)) was used.

(Reaction Device (1))

In the reaction device (1), a vertical fixed bed reactor manufactured by SUS316L (JIS standard) with 22.66 mm in inside diameter×300 mm in height was used as the reactor 2. In the reactor 2, the catalyst 5 indicated in each of the examples and comparative examples was filled at a height of 100 mm. Besides, an inside of the reactor 2 was heated by an electric furnace.

The source gas supply line 7 connected to the reactor 2 at the inlet side was heated to be in a range of 100° C. to 140° C. by a ribbon heater. It was configured such that HFC-134a being the HFC (1) and the fluorine-containing compound (Q) being the diluent gas were each adjusted in flow rate by a mass flow controller provided at the HFC supply line 8 and a syringe pump (illustration is omitted) at the fluorine-containing compound supply line 9 to be mixed, and then supplied to the preheating mixer 6.

The reactor outlet line 10 connected to the reactor 2 at the outlet side was heated to be in a range of 100° C. to 140° C. by a ribbon heater, and connected to the fluorine-containing compound trap 4. A refrigerant was circulated at the outside of the fluorine-containing compound trap 4 to keep the fluorine-containing compound trap 4 to 4° C. at an atmospheric pressure, to thereby perform heat removal of the outlet gas flowed out from the reactor 2. The outlet line 11 connected to the fluorine-containing compound trap 4 at the outlet side was connected to the hydrogen fluoride trap 3 accommodating 20 mass % of potassium hydroxide aqueous solution. The outlet line 12 connected to the hydrogen fluoride trap 3 at the outlet side was connected to the dehydrator 13 where 120 g of molecular sieves 3 A in a pellet state (manufactured by Junsei Chemical Co., Ltd., ⅛ inch pellet) were filled. Further, it was configured such that the second gas composition passed through the dehydrator 13 was collected by the sampling bag 14 made of polyvinylidene fluoride (PVdF) connected to the dehydrator 13, and thereafter, composition analysis of the second gas composition was carried out with the analyzer 15.

<Analysis Conditions>

In the analyzer 15 (GC-2010A, manufactured by SHIMADZU CORPORATION), the GC was used for the composition analysis of the second gas composition. As a column, DB-1 (manufactured by Agilent Technologies Co., Ltd., 60 m in length×250 μm in inside diameter×1 μm in thickness) was used. As a detector, a flame ionization detector (FID) was used.

<Linear Velocity>

A linear velocity means a superficial velocity, and it was calculated by assuming that the reactor which makes the source gas pass therethrough was an empty tower where filling materials were not filled therein, and dividing a flow rate (volume flow rate) by a cross-sectional area of the reactor being the empty tower. Note that experiments were performed by setting this linear velocity to 1 cm/s.

Linear velocity (superficial velocity) (cm/s)=flow rate (cm$^3$/s)/cross-sectional area (cm$^2$)

Example 1

The reactor 2 of the reaction device (1) was filled with 40 g of alumina catalyst (Al$_2$O$_3$, manufactured by JGC Catalysts and Chemicals Ltd., product name: ACBM-1, shape: spherical shape with a particle size of 2 mm), then it was heated at 350° C. for 48 hours while supplying nitrogen gas at 300 mL/min to be dried.

Next, a temperature in the reactor 2 was set to 350° C., and mixed gas where 20 mol % of HFC-134a and 80 mol % of nitrogen were mixed was supplied to the reactor 2 at the linear velocity of 1 cm/s. HFC-134a and nitrogen were continuously flowed, and then it was verified, after eight hours, that a composition of outlet gas passed through the hydrogen fluoride trap 3 was stabilized.

Next, the temperature in the reactor 2 was set to 350° C., and 20 mol % of HFC-134a and 80 mol % of perfluorohexane C$_6$F$_{14}$ (with a concentration of the number of fluorine atoms (element concentration) of 78.68%) as the fluorine-containing compound (Q) being the diluent gas were mixed to be supplied to the reactor 2. HFC-134a and the fluorine-containing compound (Q) were continuously flowed, and then it was verified that a composition of outlet gas passed through the hydrogen fluoride trap 3 was stabilized. Next, the outlet gas passed through the hydrogen fluoride trap 3 was supplied to the dehydrator 13, and after a composition of outlet gas passed through the fluorine-containing compound trap 4, the hydrogen fluoride trap 3, and the dehydrator 13 (hereinafter, it is referred to as "trap passing outlet gas") was stabilized, a sample of the outlet gas was collected every two hours. Note that a room temperature at the time of collecting the sample was 15° C.

Based on a molar ratio (mol %) of each component in the trap passing outlet gas obtained by the analysis of GC, a conversion ratio of HFC-134a and selectivity of HFO-1123 were each determined in the following manner.

In the following expressions, (HFC-134a)$_{in}$, (HFC-134a)$_{out}$, (HFO-1123)$_{out}$ and (total)$_{out}$ respectively represent molar ratios calculated from a GC area ratio of HFC-134a in the source gas, HFC-134a in the trap passing outlet gas except the diluent gas, HFO-1123 in the trap passing outlet gas, and total trap passing outlet gas components (note that although some components of the fluorine-containing compound (Q) are sometimes detected, those components were excluded). Incidentally, in this example, the calculation was performed while assuming that (HFC-134a)$_{in}$=(total)$_{out}$.

Note that the molar ratio of each component in the trap passing outlet gas was calculated by multiplying an area ratio of each component identified by GC by a detection sensitivity factor measured by using a reference material whose composition ratio is already known. Besides, the molar ratio between HFC-134a and the fluorine-containing compound (Q) in the source gas was calculated from a flow rate ratio between HFC-134a and the fluorine-containing compound (Q).

[Conversion Ratio of HFC-134a (Mol %)]

The conversion ratio of HFC-134a means a ratio of HFC-134a which is converted into other components including HFO-1123 and consumed due to the reaction. The conversion ratio of HFC-134a is calculated by the following expression.

Conversion ratio of HFC-134a (mol %)={1−(HFC-134a)$_{out}$/(HFC-134a)$_{in}$}×100

[Selectivity of HFO-1123 (Mol %)]

The selectivity of HFO-1123 means a ratio converted into HFO-1123 among the reacted HFC-134a. The selectivity of HFO-1123 is calculated by the following expression.

Selectivity of HFO-1123 (mol %)=(HFO-1123)$_{out}$/{1−(HFC-134a)$_{out}$/(HFC-134a)$_{in}$}×100

Note that these results were each an average value of analyses of samples which were collected from when the reaction was stabilized to when the reaction finished.

Calculation results of the conversion ratio of HFC-134a and the selectivity of HFO-1123 are shown in Table 1 together with reaction conditions (HFC-134a flow rate (mol %), fluorine-containing compound (Q) flow rate (mol %) which are supplied to the reactor, and temperature in the reactor (° C.)). Further, a normal boiling point difference between the fluorine-containing compound (Q) used in the example 1 and the obtained HFO (2) (=normal boiling point of fluorine-containing compound (Q)—normal boiling point of HFO (2)) is shown in the right column of Table 1. Also in Tables 2 to 4 to be shown below, the normal boiling point difference between the fluorine-containing compound (Q) and the HFO (2) is shown in a similar manner.

Note that the temperature in the reactor is the temperature in the reactor 2, and it is an actual measured value. Besides, the linear velocity is the linear velocity of the source gas supplied to the reactor.

Examples 2 to 4

The reactions were continuously carried out similarly to the example 1 except that the reaction conditions and the kind of the fluorine-containing compound (Q) were changed as shown in Table 1. Subsequently, the conversion ratio of HFC-134a and the selectivity of HFO-1123 were respectively determined similarly to the example 1. Obtained results are shown in Table 1. As the fluorine-containing compound (Q), $C_6F_{14}$ or ethyl perfluorobutyl ether $C_4F_9OC_2H_5$ (with a concentration of the number of fluorine atoms (element concentration) of 64.75%) was used.

Examples 5, 6

The reactions were continuously carried out similarly to the example 1 except that the reactor 2 of the reaction device (1) was filled with 40 g of aluminum trifluoride ($AlF_3$, manufactured by Kanto Chemical Co., Inc., product name: Aluminum Trifluoride, shape: powder), and the reaction conditions were changed as shown in Table 1. Subsequently, the conversion ratio of HFC-134a and the selectivity of HFO-1123 were respectively determined similarly to the example 1. Obtained results are shown in Table 1.

Examples 7, 8

The reactions were continuously carried out similarly to the example 1 except that the reactor 2 of the reaction device (1) was filled with 50 g of zirconium dioxide ($ZrO_2$, manufactured by Kanto Chemical Co., Inc., product name: Zirconium oxide, shape: pellet), and the reaction conditions were changed as shown in Table 2. Subsequently, the conversion ratio of HFC-134a and the selectivity of HFO-1123 were respectively determined similarly to the example 1. Obtained results are shown in Table 2.

Examples 9, 10

The reactions were continuously carried out similarly to the example 1 except that the reactor 2 of the reaction device (1) was filled with 45 g of aluminum oxide on which 5 mass % of palladium was supported ($Pd/Al_2O_3$, manufactured by Junsei Chemical Co., Ltd., shape: pellet), and the reaction conditions were changed as shown in Table 2. Subsequently, the conversion ratio of HFC-134a and the selectivity of HFO-1123 were respectively determined similarly to the example 1. Obtained results are shown in Table 2.

Example 11

The reactions were continuously carried out similarly to the example 1 except that the composition of the source gas and the reaction conditions were changed as shown in Table 3. Subsequently, the conversion ratio of HFC-245eb and the selectivity of HFO-1234yf were calculated based on the following expressions.

In the following expressions used in the calculation, $(HFC\text{-}245eb)_{in}$, $(HFC\text{-}245eb)_{out}$, $(HFO\text{-}1234yf)_{out}$ and $(total)_{out}$ respectively represent molar ratios calculated from a GC area ratio of HFC-245eb in the source gas, HFC-245eb in the trap passing outlet gas except the diluent gas, HFO-1234yf in the trap passing outlet gas, and total trap passing outlet gas components (note that although there is a case where the fluorine-containing compounds (Q) are partially detected, those were excluded). Incidentally, in this example, the calculation was performed while assuming that $(HFC\text{-}245eb)_{in}=(total)_{out}$. Obtained results are shown in Table 3.

Conversion ratio of HFC-245*eb* (mol %)=
    $\{1-(HFC\text{-}245eb)_{out}/(HFC\text{-}245eb)_{in}\}\times 100$ Selectivity of HFO-1234*yf* (mol %)=
    $(HFO\text{-}1234yf)_{out}/\{1-(HFC\text{-}245eb)_{out}/(HFC\text{-}245eb)_{in}\}\times 100$

Example 12

The reactions were continuously carried out similarly to the example 1 except that the composition of the source gas and the reaction conditions were changed as shown in Table 4. Subsequently, the conversion ratio of HFC-245cb and the selectivity of HFO-1234yf were calculated from the following expressions.

In the following expressions used in the calculation, $(HFC\text{-}245cb)_{in}$, $(HFC\text{-}245cb)_{out}$, $(HFO\text{-}1234yf)_{out}$ and $(total)_{out}$ respectively represent molar ratios calculated from a GC area ratio of HFC-245cb in the source gas, HFC-245cb in the trap passing outlet gas, HFO-1234yf in the trap passing outlet gas, and total trap passing outlet gas components (note that although there is a case where the fluorine-containing compounds (Q) are partially detected, those were excluded). Incidentally, in this example, the calculation was performed while assuming that $(HFC\text{-}245cb)_{in}=(total)_{out}$. Obtained results are shown in Table 4.

Conversion ratio of HFC-245*cb* (mol %)=
    $\{1-(HFC\text{-}245cb)_{out}/(HFC\text{-}245cb)_{in}\}\times 100$ Selectivity of HFO-1234*yf* (mol %)=
    $(HFO\text{-}1234yf)_{out}/\{1-(HFC\text{-}245cb)_{out}/(HFC\text{-}245cb)_{in}\}\times 100$

Comparative Examples 1 to 8

The reactions were continuously carried out similarly to the example 1 except that the composition of the source gas and the reaction conditions were changed as shown in Table 5. Subsequently, the conversion ratio of HFC-134a and the selectivity of HFO-1123 were respectively determined similarly to the example 1. Obtained results are shown in Table 5. Note that as the diluent gas, nitrogen gas was used in place of the fluorine-containing compound (Q).

TABLE 1

| | Fluorine-containing compound (Q) Kind | Catalyst Kind | Flow rate HFC-134a (mol %) | Fluorine-containing compound (Q) (mol %) | Temperature in reactor (° C.) | Conversion ratio of HFC-134a (%) | Selectivity of HFO-1123 (%) | Normal boiling point difference (° C.) |
|---|---|---|---|---|---|---|---|---|
| Example 1 | $C_6F_{14}$ | $Al_2O_3$ | 20 | 80 | 350 | 7.8 | 98.7 | 112.6 |
| Example 2 | $C_6F_{14}$ | $Al_2O_3$ | 20 | 80 | 400 | 23.8 | 99.5 | |

TABLE 1-continued

| | Fluorine-containing compound (Q) Kind | Catalyst Kind | Flow rate HFC-134a (mol %) | Flow rate Fluorine-containing compound (Q) (mol %) | Temperature in reactor (° C.) | Conversion ratio of HFC-134a (%) | Selectivity of HFO-1123 (%) | Normal boiling point difference (° C.) |
|---|---|---|---|---|---|---|---|---|
| Example 3 | $C_6F_{14}$ | $Al_2O_3$ | 5 | 95 | 450 | 43.6 | 97.4 | |
| Example 4 | $C_4F_9OC_2H_5$ | $Al_2O_3$ | 20 | 80 | 400 | 18.5 | 95.3 | 132 |
| Example 5 | $C_6F_{14}$ | $AlF_3$ | 20 | 80 | 400 | 10.3 | 98.5 | 112.6 |
| Example 6 | $C_6F_{14}$ | $AlF_3$ | 5 | 95 | 500 | 25.5 | 97.1 | |

TABLE 2

| | Fluorine-containing compound (Q) Kind | Catalyst Kind | Flow rate HFC-134a (mol %) | Flow rate Fluorine-containing compound (Q) (mol %) | Temperature in reactor (° C.) | Conversion ratio of HFC-134a (%) | Selectivity of HFO-1123 (%) | Normal boiling point difference (° C.) |
|---|---|---|---|---|---|---|---|---|
| Example 7 | $C_6F_{14}$ | $ZrO_2$ | 5 | 95 | 350 | 12.4 | 99.1 | 112.6 |
| Example 8 | $C_6F_{14}$ | $ZrO_2$ | 20 | 80 | 400 | 9.8 | 99.0 | |
| Example 9 | $C_6F_{14}$ | $Pd/Al_2O_3$ | 20 | 80 | 400 | 24.5 | 97.6 | |
| Example 10 | $C_6F_{14}$ | $Pd/Al_2O_3$ | 5 | 95 | 400 | 35.5 | 98.0 | |

TABLE 3

| | Fluorine-containing compound (Q) Kind | Catalyst Kind | Flow rate HFC-245eb (mol %) | Flow rate $C_6F_{14}$ (mol %) | Temperature in reactor (° C.) | Conversion ratio of HFC-245eb (%) | Selectivity of HFO-1234yf (%) | Normal boiling point difference (° C.) |
|---|---|---|---|---|---|---|---|---|
| Example 11 | $C_6F_{14}$ | $Al_2O_3$ | 5 | 95 | 400 | 78.5 | 95.4 | 84.9 |

TABLE 4

| | Fluorine-containing compound (Q) Kind | Catalyst Kind | Flow rate HFC-245cb (mol %) | Flow rate $C_6F_{14}$ (mol %) | Temperature in reactor (° C.) | Conversion ratio of HFC-245cb (%) | Selectivity of HFO-1234yf (%) | Normal boiling point difference (° C.) |
|---|---|---|---|---|---|---|---|---|
| Example 12 | $C_6F_{14}$ | $Al_2O_3$ | 5 | 95 | 400 | 70.1 | 96.3 | 84.9 |

TABLE 5

| | Catalyst Kind | Flow rate HFC-134a (mol %) | Flow rate $N_2$ (mol %) | Temperature in reactor (° C.) | Conversion ratio of HFC-134a (%) | Selectivity of HFO-1123 (%) |
|---|---|---|---|---|---|---|
| Comparative Example 1 | $Al_2O_3$ | 20 | 80 | 350 | 5.7 | 98.7 |
| Comparative Example 2 | $Al_2O_3$ | 5 | 95 | 350 | 12.4 | 94.5 |
| Comparative Example 3 | $Al_2O_3$ | 5 | 95 | 400 | 35.5 | 98.3 |
| Comparative Example 4 | $Al_2O_3$ | 20 | 80 | 400 | 18.9 | 94.5 |
| Comparative Example 5 | $Al_2O_3$ | 20 | 80 | 450 | 39.6 | 94.4 |
| Comparative Example 6 | $Al_2O_3$ | 10 | 90 | 450 | 56.2 | 95.1 |
| Comparative Example 7 | $Al_2O_3$ | 5 | 95 | 450 | 61.9 | 92.2 |
| Comparative Example 8 | $Al_2O_3$ | 5 | 95 | 500 | 75.5 | 73.4 |

As it can be seen from Tables 1 to 5, when compared to the comparative examples 1 to 8 where nitrogen was used as the diluent gas, each of the examples 1 to 12 where the fluorine-containing compound (Q) was used as the diluent gas had the nearly equal selectivity, although the conversion ratio thereof was slightly inferior. Further, as it can be seen from Tables 1 to 5, the conversion ratio of HFC-134a becomes high as the molar ratio of HFC-134a in the source gas becomes smaller or the temperature in the reactor becomes higher.

Example 13

There was used a device similar to the reaction device (1) used in the example 1 except that a hydrogen fluoride trap 3 filled with NaF was used as the hydrogen fluoride trap 3, and the hydrogen fluoride trap 3 was arranged between the reactor 2 and the fluorine-containing compound trap 4. Operations similar to those of the example 1 were performed except that the heat removal conditions of the fluorine-containing compound trap 4 were changed to an atmospheric pressure and a room temperature (about 4 to 15° C.) among the conditions in the example 1, and $C_6F_{14}$ flowed out from the hydrogen fluoride trap 3 was recovered into the fluorine-containing compound trap 4 which was let stand at a room temperature. The mass of $C_6F_{14}$ supplied to the reactor 2 and the mass of $C_6F_{14}$ recovered at the fluorine-containing compound trap 4 were 215.6 g and 208.2 g, respectively. From the above result, a separation ratio, through the heat removal, of $C_6F_{14}$ used as the diluent gas was 95% or more.

From the above, it was confirmed that the fluorine-containing compound (Q) used as the diluent gas in the method of the present embodiment can be separated through the heat removal.

Comparative Example 9

In the operation in the comparative example 6, gas flow rates of the source gas supply line and the diluent gas supply line and a gas flow rate after passage of the hydrogen fluoride trap 3 were measured by using a dry gas meter (manufactured by Shinagawa Corporation). As a result of this, the gas flow rate calculated from a total gas flow rate of the source gas and diluent gas supply lines was 0.264 mol/h, and the gas flow rate after the passage of the hydrogen fluoride trap 3 was 0.262 mol/h. From the above result, it can be understood that it is difficult to separate $N_2$ used as the diluent gas through the heat removal.

According to the method of producing HFO of the present embodiment, it is possible to efficiently and stably manufacture HFO from HFC. Besides, the fluorine-containing compound (Q) being diluent gas can be separated and recovered to be reused, which is useful as an industrial producing method.

What is claimed is:

1. A method of producing a hydrofluoroolefin of formula (2), comprising:
   converting a hydrofluorocarbon of formula (1) into the hydrofluoroolefin of the formula (2) in the presence of a fluorine-containing compound having a normal boiling point higher than a normal boiling point of the hydrofluoroolefin of the formula (2) to obtain a first gas composition containing the hydrofluoroolefin and the fluorine-containing compound,

   $$CR^1R^2X^1CR^3R^4X^2 \quad (1)$$

   $$CR^1R^2=CR^3R^4 \quad (2)$$

wherein, in the formula (1) and the formula (2), $R^1$ to $R^3$ are each independently a hydrogen atom or a fluorine atom, $R^4$ is a hydrogen atom, a fluorine atom, $CH_3$, $CH_2F$, $CHF_2$ or $CF_3$, the total number of fluorine atoms of $R^1$ to $R^4$ is one or more, and the total number of hydrogen atoms of $R^1$ to $R^4$ is one or more, and one of $X^1$ and $X^2$ is a hydrogen atom, and the other of $X^1$ and $X^2$ is a fluorine atom; and
   separating the fluorine-containing compound from the first gas composition to obtain a second gas composition containing the hydrofluoroolefin, wherein
   the fluorine-containing compound is inert and in a gaseous state while the hydrofluorocarbon of the formula (1) is converted into the hydrofluoroolefin of the formula (2),
   the fluorine-containing compound comprises a carbon atom and a fluorine atom, and
   the number of fluorine atoms and the number of carbon atoms in the fluorine-containing compound satisfy formula: $m \leq n \leq 2m+2$, provided that n is the number of the fluorine atoms and m is the number of the carbon atoms,
   wherein:
   the fluorine-containing compound is a compound in which a part of or all of hydrogen atoms of:
   a saturated or unsaturated hydrocarbon compound having a carbon number of 4 to 10; or
   a saturated or unsaturated organic compound having at least one or more of hetero atoms selected from the group consisting of an oxygen atom, a sulfur atom, a selenium atom, and a nitrogen atom at a position between a carbon atom and a carbon atom of the hydrocarbon compound,
   are substituted with fluorine atoms;
   there is no case where, out of two adjacent carbons in the fluorine-containing compound, one has a carbon-fluorine bond and the other has a carbon-hydrogen bond; and
   the number of fluorine atoms contained in the fluorine-containing compound is 45% or more in terms of element concentration in the fluorine-containing compound.

2. The method according to claim 1, wherein
   a difference between the normal boiling point of the fluorine-containing compound and the normal boiling point of the hydrofluoroolefin is 10° C. or more.

3. The method according to claim 1, wherein
   the fluorine-containing compound comprises at least one selected from the group consisting of a perfluorocarbon, a perfluoroalkyl ether, an alkyl perfluoroalkyl ether, a perfluoroalkyl thioether, an alkyl perfluoroalkyl thioether, a perfluoroalkene, and a perfluoroaromatic compound.

4. The method according to claim 1, wherein
   the fluorine-containing compound comprises at least one selected from the group consisting of perfluoropentane, perfluoro-2-methylpentane, perfluorohexane, perfluoro-2-methylhexane, perfluoroheptane, perfluorocyclohexane, perfluoromethylcyclohexane, perfluorobenzene, perfluorotoluene, perfluoroethyl perfluorobutyl ether, perfluoroethyl perfluoropentyl ether, ethyl perfluorobutyl ether, propyl perfluorobutyl ether, and ethyl perfluoropentyl ether.

5. The method according to claim 1, wherein
   the fluorine-containing compound is separated from the first gas composition by liquefying the fluorine-containing compound under a pressure of not less than −0.1 MPa nor more than 4.0 MPa and a temperature of not less than −30° C. nor more than 100° C.

6. The method according to claim 1, wherein
   a molar ratio of the hydrofluorocarbon to the fluorine-containing compound is not less than 0.5/99.5 nor more than 60/40, when the hydrofluorocarbon and the fluorine-containing compound are supplied to a rector for converting the hydrofluorocarbon.

7. The method according to claim 1, wherein
   the hydrofluorocarbon is 1,1,1,2-tetrafluoroethane, and the hydrofluoroolefin is trifluoroethylene.

8. The method according to claim 1, wherein
   the hydrofluorocarbon is 1,1,1,2,2-pentafluoropropane and/or 1,1,1,2,3-pentafluoropropane, and the hydrofluoroolefin is 2,3,3,3-tetrafluoropropene.

9. The method according to claim 1, wherein
the hydrofluorocarbon and a catalyst are brought into contact with each other when the hydrofluorocarbon of the formula (1) is converted into the hydrofluoroolefin of the formula (2).

10. The method according to claim 9, wherein
the catalyst contains at least one selected from the group consisting of a metal, a metal oxide, and a metal halide.

11. The method according to claim 9, wherein
the catalyst comprises at least one selected from the group consisting of iron, zinc, cobalt, nickel, palladium, platinum, iridium, rhodium, ruthenium, chromium oxide, aluminum oxide, zinc oxide, zirconium oxide, niobium oxide, tin oxide, titanium oxide, iron oxide fluoride, aluminum fluoride, aluminum chloride, chromium fluoride, chromium chloride, and silicon oxide.

12. The method according to claim 1, wherein
a temperature to convert the hydrofluorocarbon into the hydrofluoroolefin is not less than 200° C. nor more than 1200° C.

13. The method according to claim 1, wherein a difference between the normal boiling point of the fluorine-containing compound and the normal boiling point of the hydrofluoroolefin is 20° C. or more.

14. The method according to claim 1, wherein a difference between the normal boiling point of the fluorine-containing compound and the normal boiling point of the hydrofluoroolefin is 40° C. or more.

15. The method according to claim 1, wherein a molar ratio of the hydrofluorocarbon to the fluorine-containing compound is not less than 05/95 nor more than 50/50, when the hydrofluorocarbon and the fluorine-containing compound are supplied to a rector for converting the hydrofluorocarbon.

16. The method according to claim 9, wherein the catalyst comprises at least one selected from the group consisting of a metal oxide and a metal halide.

17. The method according to claim 1, wherein the fluorine-containing compound is separated from the first gas composition by liquefying the fluorine-containing compound under a pressure of not less than −0.1 MPa nor more than 2.0 MPa and a temperature of not less than −10° C. nor more than 100° C.

18. The method according to claim 1, wherein the fluorine-containing compound is separated from the first gas composition by liquefying the fluorine-containing compound under a pressure of not less than −0.1 MPa nor more than 0.02 MPa and a temperature of not less than 0° C. nor more than 90° C.

* * * * *